United States Patent
Ortiz et al.

(10) Patent No.: US 7,618,427 B2
(45) Date of Patent: Nov. 17, 2009

(54) DEVICE AND METHOD FOR INTRALUMENAL ANASTOMOSIS

(75) Inventors: Mark S. Ortiz, Milford, OH (US); Rudolph H. Nobis, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 658 days.

(21) Appl. No.: 10/947,567

(22) Filed: Sep. 22, 2004

(65) Prior Publication Data
US 2005/0143763 A1 Jun. 30, 2005

Related U.S. Application Data

(63) Continuation-in-part of application No. 10/747,488, filed on Dec. 29, 2003, now abandoned.

(51) Int. Cl.
  *A61B 17/10* (2006.01)
(52) U.S. Cl. ........................... 606/142; 606/151
(58) Field of Classification Search ............... 606/206, 606/207, 139–143, 151–158
See application file for complete search history.

(56) References Cited

U.S. PATENT DOCUMENTS

| | | | | |
|---|---|---|---|---|
| 5,147,378 A | * | 9/1992 | Markham | 606/206 |
| 5,258,000 A | | 11/1993 | Gianturco | |
| 5,993,474 A | * | 11/1999 | Ouchi | 606/206 |
| 5,997,556 A | | 12/1999 | Tanner | |
| 6,086,600 A | * | 7/2000 | Kortenbach | 606/139 |
| 6,113,609 A | * | 9/2000 | Adams | 606/139 |
| 6,258,105 B1 | * | 7/2001 | Hart et al. | 606/142 |
| 6,416,522 B1 | | 7/2002 | Strecker | |
| 6,425,900 B1 | | 7/2002 | Knodel et al. | |
| 6,517,552 B1 | * | 2/2003 | Nord et al. | 606/144 |
| 6,543,456 B1 | | 4/2003 | Freeman | |
| 6,616,675 B1 | | 9/2003 | Evard et al. | |
| 6,837,893 B2 | * | 1/2005 | Miller | 606/139 |
| 6,884,248 B2 | | 4/2005 | Bolduc et al. | |
| 7,077,850 B2 | * | 7/2006 | Kortenbach | 606/151 |
| 2001/0005787 A1 | * | 6/2001 | Oz et al. | 606/142 |
| 2002/0049455 A1 | * | 4/2002 | Cummins et al. | 606/139 |

(Continued)

FOREIGN PATENT DOCUMENTS

WO WO 02/17771 3/2002

(Continued)

*Primary Examiner*—(Jackie) Tan-Uyen T. Ho
*Assistant Examiner*—Melanie Tyson
(74) *Attorney, Agent, or Firm*—Frost Brown Todd LLC

(57) ABSTRACT

An anastomosis device formed from a Shape Memory Alloy (SME) wire that is annealed into a tight coil (e.g., flat coil, helical coil, cylindrical coil) that is subsequently substantially straightened (e.g., straight, longitudinally stretched spring-like shape) for being constrained within an elongate member of an anastomosis introducer instrument. After positioning and holding two tissue walls of adjacent lumens into apposition with a distally presented grasper of the instrument, a piercing tip of the anastomosis device is dispensed and inserted through the tissue walls before being allowed to relax to its tight coil shape, thereby forming the anastomosis attachment. The anastomosis device is released from the anastomosis introducer instrument, such as by fully dispensing its proximal end. Thereby, efficient single lumen anastomosis of gastrointestinal, bilatory, or other vessels may be achieved with a minimum of laparoscopic punctures, or perhaps performed fully as an endoscopic procedure.

6 Claims, 6 Drawing Sheets

U.S. PATENT DOCUMENTS

| | | |
|---|---|---|
| 2003/0120289 A1* | 6/2003 | McGuckin et al. .......... 606/151 |
| 2004/0127919 A1* | 7/2004 | Trout et al. ................. 606/157 |
| 2004/0232197 A1 | 11/2004 | Shelton et al. |
| 2005/0070921 A1 | 3/2005 | Ortiz et al. |
| 2005/0070926 A1 | 3/2005 | Ortiz |
| 2005/0070935 A1 | 3/2005 | Ortiz |
| 2005/0070939 A1 | 3/2005 | Beaupre |
| 2006/0259050 A1 | 11/2006 | De Winter |

FOREIGN PATENT DOCUMENTS

| | | |
|---|---|---|
| WO | PCT/BE03/00074 | 4/2003 |
| WO | WO 2004/096059 | 11/2004 |
| WO | WO 2004/096337 | 11/2004 |

* cited by examiner

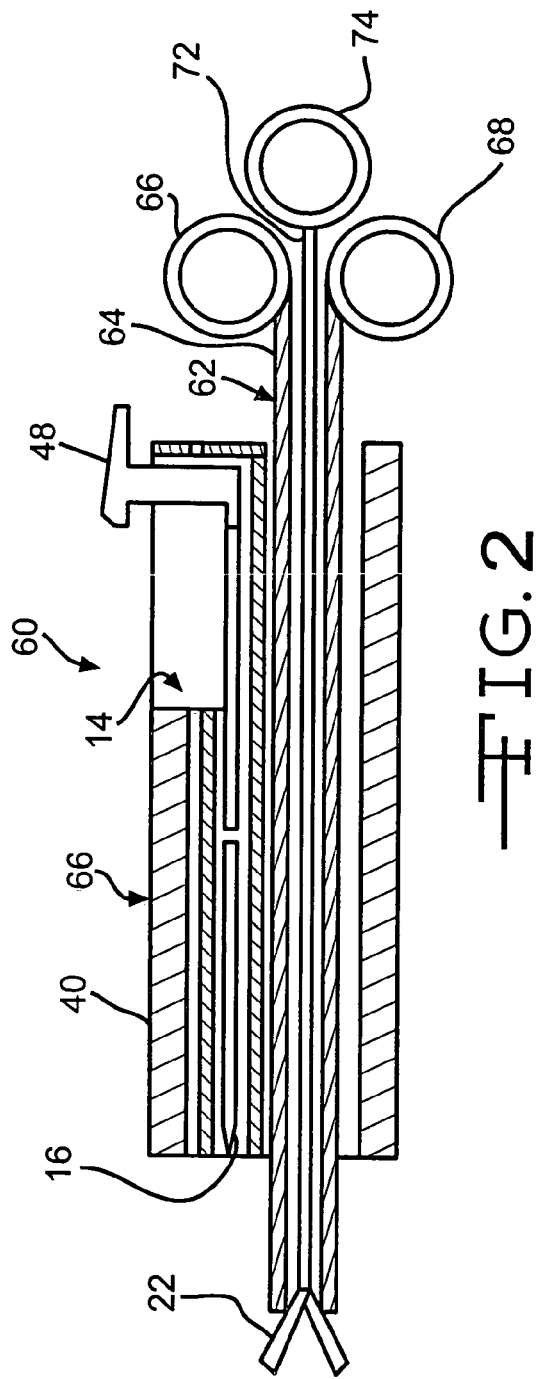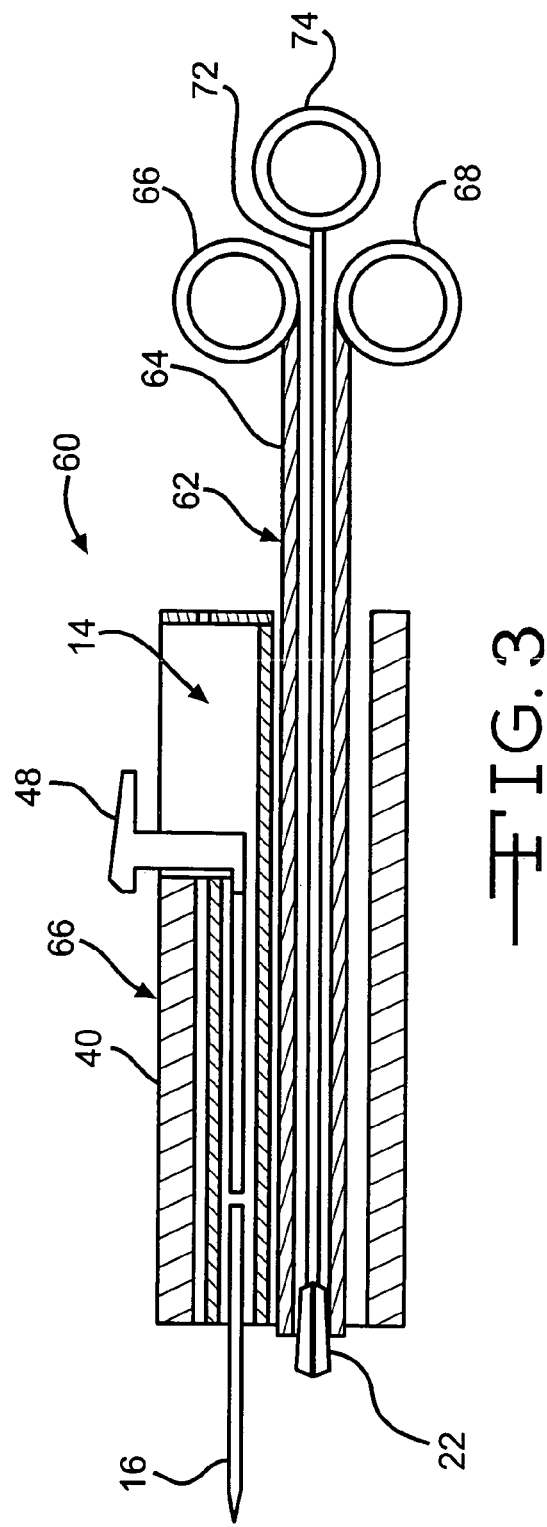

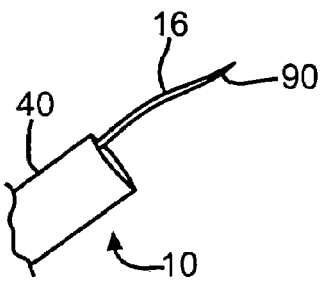
FIG. 4A
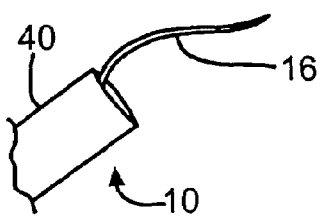
FIG. 4B
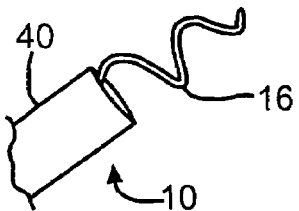
FIG. 4C
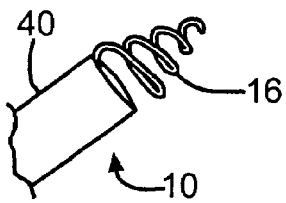
FIG. 4D
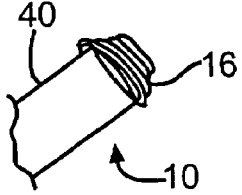
FIG. 4E
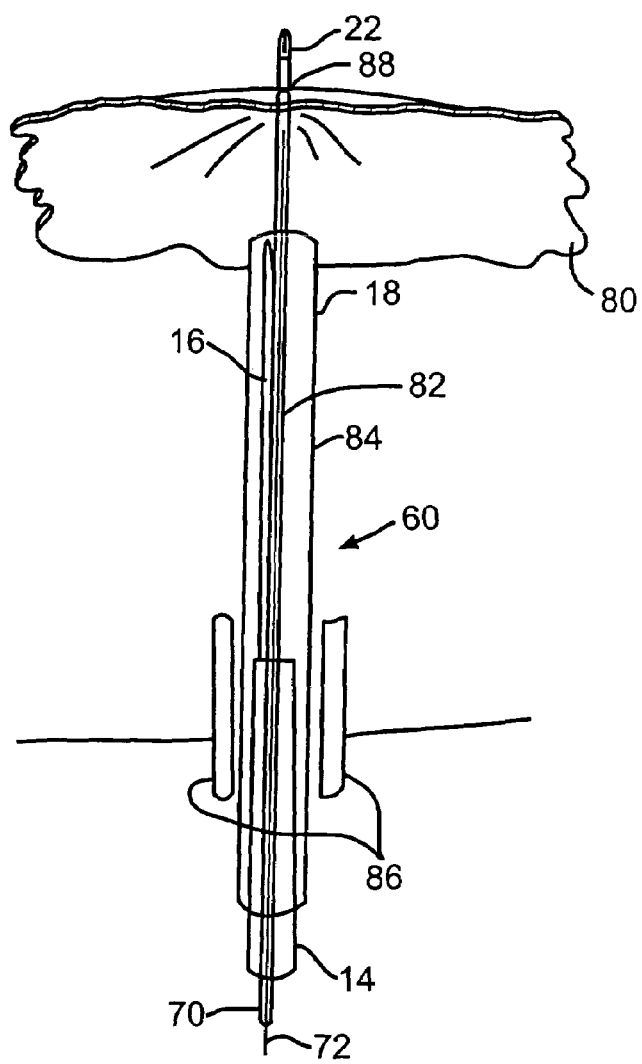
FIG. 4

DEVICE AND METHOD FOR INTRALUMENAL ANASTOMOSIS

CROSS REFERENCE TO RELATED APPLICATIONS

This is a continuation-in-part of application Ser. No. 10/747,488, filed 29 Dec. 2003, now abandoned which is incorporated herein in its entirety by reference.

FIELD OF THE INVENTION

The present invention relates, in general, to surgery and, more particularly, to a method of performing a surgical procedure between two lumens.

BACKGROUND OF THE INVENTION

The percentage of the world population suffering from morbid obesity is steadily increasing. Severely obese persons are susceptible to increased risk of heart disease, stroke, diabetes, pulmonary disease, and accidents. Because of the effect of morbid obesity to the life of the patient, methods of treating morbid obesity are being researched.

Numerous non-operative therapies for morbid obesity have been tried with virtually no permanent success. Dietary counseling, behavior modification, wiring a patient's jaws shut, and pharmacologic methods have all been tried, and, though temporarily effective, have failed to correct the condition. Further, introducing an object into the stomach, such as an esophago-gastric balloon, to fill the stomach have also been used to treat the condition; however, such approaches tend to cause irritation to the stomach and are not effective long-term.

Surgical treatments of morbid obesity have been increasingly used with greater success. These approaches may be generalized as those that reduce the effective size of the stomach, limiting the amount of food intake, and those that create malabsorption of the food that is eaten. For instance, some patients benefit from adjustable gastric bands (AGB) that are advantageously laparoscopically placed about the stomach to form a stoma of a desired size that allows food to fill an upper portion of the stomach, causing a feeling of satiety. To allow adjustment of the size of the stoma after implantation, a fluid conduit communicates between an inwardly presented fluid bladder of the AGB to a fluid injection port subcutaneously placed in front of the patient's sternum. A syringe needle may then inject or withdraw fluid as desired to adjust the AGB.

Although an effective approach to obesity for some, other patients may find the lifestyle changes undesirable, necessitated by the restricted amount of food intake. In addition, the medical condition of the patient may suggest the need for a more permanent solution. To that end, surgical approaches have been used to alter the portions of the stomach and/or small intestine available for digesting food. Current methods of performing a laparoscopic anastomosis for a gastric bypass include stapling, suturing, and placing biofragmentable rings, each having significant challenges. For example, suturing is time consuming, as well as technique and dexterity dependent. Stapling requires placement of an anvil, which is a large device that may not be introduced through a trocar port. Introducing the port through a laparotomy presents an increased incidence of wound site infection associated with intralumenal content being dragged to the laparotomy entry site.

As an example of the latter approach, U.S. Pat. No. 6,543,456 discloses a method for gastric bypass surgery that includes the insertion of proximal and distal anastomosis members (e.g., anvils) transorally with grasping forceps. The stomach and the small intestine are transected endoscopically by a surgical severing and stapling instrument to create a gastric pouch, a drainage loop, and a Roux limb. An endoscopically inserted circular stapler attaches to the distal anastomosis member to join the drainage loop to a distal portion of the intestine, and the circular stapler attaches to the proximal anastomosis member to join the Roux limb to the gastric pouch. Thereafter, the anastomosis members are removed to create an orifice between joined portions of the stomach and intestine. This method reduces the number of laparoscopic ports, avoids a laparoscopic insertion of an anastomosis instrument (e.g., circular stapler) into an enlarged sugical port, and eliminates the need for an enterotomy and an enterotomy closure.

While methods such as those described are a marked improvement over generally known gastric bypass and similar surgical treatments for morbid obesity, it would be desirable to achieve a gastric bypass with yet fewer procedural steps and fewer laparoscopic insertions. Such an approach is described in U.S. Pat. Appl. Publ. No. U.S. 2003/0032967 to Park et al., wherein gastrointestinal or enteric (including biliary) anastomosis is achieved by insertion of a sheath that perforates the walls of two tissue passages, such as the stomach and small intestine. A three-dimensional woven tube of wire having a thermal shape memory effect (SME) ("nitinol Park device") is presented by a cannula of the sheath on both sides of the openings. Deployment of the woven tube causes the outer loops or ends of the tube to fold or loop back to hold the luminal interface of the anastomosis site in apposition (close?). Thereby, the need for a mechanical compression component in a delivery system is reduced or avoided, reducing the size and complexity of the delivery device.

While the nitinol Park device is an advancement in the treatment of morbid obesity, it is believed that further improvements would be desirable. The Park device is a woven tube, or stent, that is purported to be a self-actuating anastomotic ring. However, the disclosed stent performs poorly in actuating or transforming from its stressed cylindrical state to its relaxed clamping state. Often, the stent remains stuck in the cylindrical shape after deployment, perhaps due to irregularities in undulations of its woven design that create friction. One particular difficulty of known SME anastomotic rings are that they are designed to move from a generally cylindrical shape to a hollow rivet shape ("ring shape") by having wires that form the device move across one another. In particular, wires must move within a nodal point (i.e., an indentation or valley) created by the wire bend and must climb back out of the indentation. In some instances, the device fails to fully actuate on its own due to these sources of friction.

Consequently, there is a general need for an approach to creating an anastomosis for surgical procedures (e.g., gastrojejeunostomies, etc.) that may be performed with a minimum number of transcutaneous punctures, which allows for the anastomosis procedure to potentially be performed on an out-patient basis. There is a further need for an anastomosis approach, which provides an anastomosis device that may fully and accurately deploy at an anastomotic site between multiple lumens.

BRIEF SUMMARY OF THE INVENTION

The invention overcomes the above-noted and other deficiencies of the prior art by providing an introducer instrument that intralumenally deploys an anastomosis device formed of Shape Memory Alloy (SMA) that presents a distally pointed end to pierce apposite tissue walls and that forms coils that engage the tissue walls, collapsing into a relaxed, tightly coiled shape (e.g., flat coil, cylindrical coil, helical coil) that thereby forms an anastomosis. Thereby, a medical procedure may be readily performed with a minimum number of laparoscopic punctures, and perhaps even solely by endoscopic means.

In one aspect of the invention, an anastomosis device is formed of SMA wire that is shaped into a tight coil and which is then heated at an annealing temperature as required to create a Shape Memory Effect (SME) at this tightly coiled (relaxed) shape. Thereafter, the SMA wire is formed into a substantially straightened (stressed) shape to present a piercing tip that may be inserted through the tissue walls with longitudinally spaced coils formed, either before or after insertion, that subsequently substantially collapse longitudinally after insertion across both tissue walls to form an anastomosis.

In another aspect of the invention, an anastomosis introducer instrument includes an elongate member inserted proximally to two tissue walls of two lumens. The anastomosis device is initially constrained within the elongate member in its substantially straightened (stressed) shape until a dispensing member distally dispenses the anastomosis device to present its piercing tip for insertion through the two tissue walls. Thereafter, the anastomosis introducer instrument releases the anastomosis device, which relaxes to its tight coil relaxed shape to form the anastomosis attachment.

In yet another aspect of the invention, an anastomosis introducer instrument includes an outer sheath that contains a distally open recess constraining the substantially straightened (stressed) anastomosis device. A deployment member is longitudinally slidingly received proximal to the distally open recess to expel the anastomosis device. A gripping member distally presented from the outer sheath is responsive to a closing motion transferred through the outer sheath to selectively close for positioning the tissue lumens. This combination thus provides a single instrument capable of performing an anastomosis without requiring a separate grasping instrument to be used to position and hold the tissue walls in apposition.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 2 is a left side diagrammatic view in cross section of an anastomosis instrument similar to FIG. 1 but with a separately positionable grasping mechanism depicted as distally extended and open.

FIG. 3 is a left side diagrammatic view of the anastomosis instrument of FIG. 2 depicted with the grasping mechanism drawn proximally and closed and with the anastomosis device extrusion mechanism having been partially actuated to extrude the anastomosis device.

FIG. 4 is a perspective view in cross section of the anastomosis instrument of FIG. 2 being inserted through a trocar to an anastomosis site of tissue walls of a proximal lumen and a distal lumen to deploy and engage a coiling anastomosis device, or clamp.

FIGS. 4A-4E are a sequence of perspective views of a distal end of the anastomosis instrument dispensing an initially straightened anastomosis device that presents a piercing tip for being inserted through the tissue walls and that coils and longitudinally collapses to its annealed, tightly coiled relaxed shape to engage the tissue walls.

DETAILED DESCRIPTION OF THE INVENTION

Figure 1:
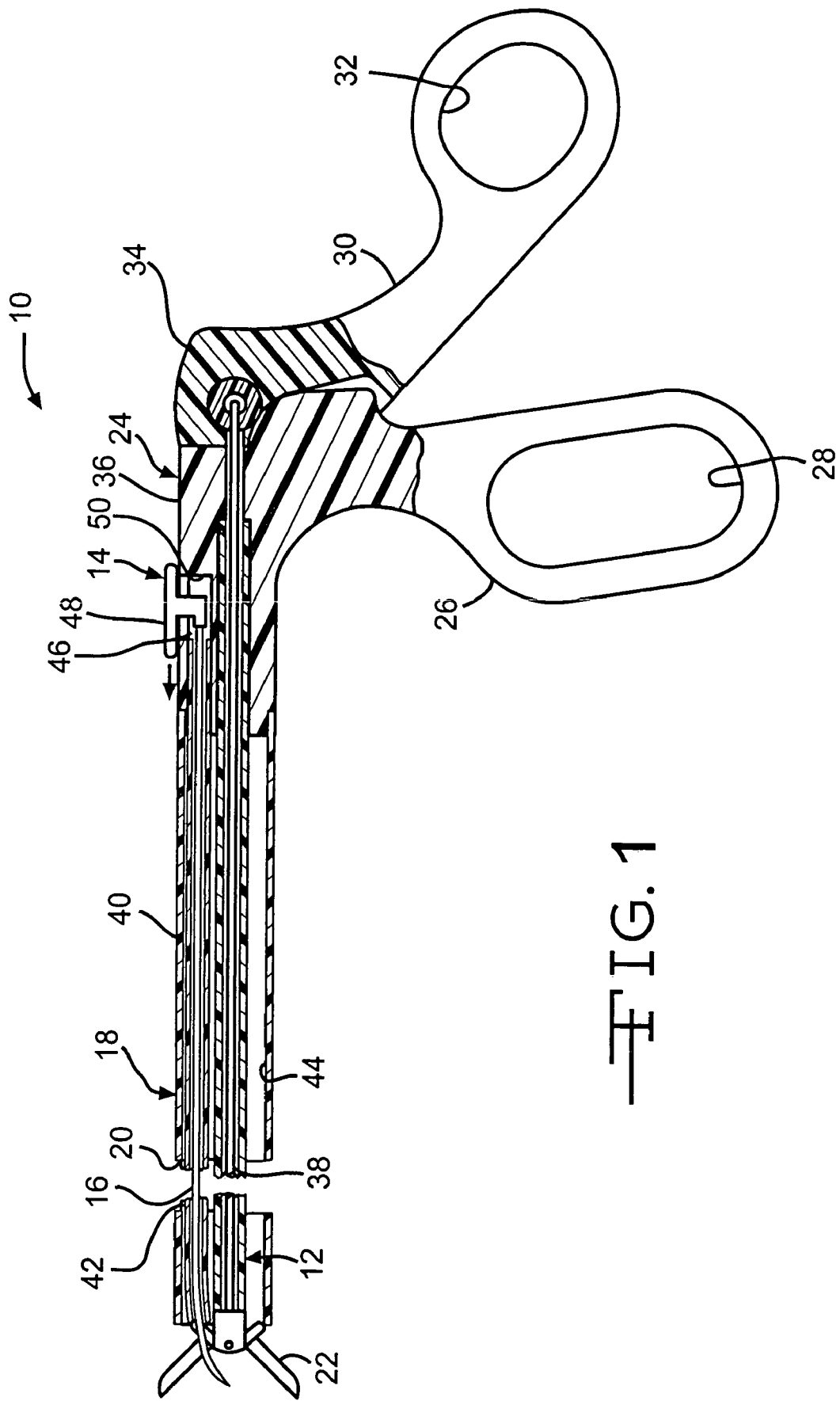
FIG. 1 is a left side view in cross section of an anastomosis instrument to a grasping mechanism and an anastomosis device extrusion mechanism.

Turning to the drawings, wherein like numerals denote like components throughout the several views, in FIG. 1, an anastomosis instrument 10 advantageously incorporates both a grasping mechanism 12 as well as an extrusion mechanism 14 for dispensing a straightened anastomosis device ("clamp") 16 for piercing two tissue walls (not shown in FIG. 1) of adjacent lumens. The anastomosis device 16 is formed of a Shape Memory Alloy (SMA) that was annealed into a flattened coil and then straightened. After dispensing, the anastomosis device 16 thereafter responds to no longer being constrained by the anastomosis instrument 10 and by being warmed by body heat. Thereafter, tightened coils are formed to provide an accurate and consistent anastomosis with a patent lumen in an endoscopic setting, perhaps obviating the need for laparoscopic punctures.

In the version of the anastomosis instrument 10 depicted in FIG. 1, the grasping mechanism 12 is similar to generally known graspers or forceps that include an elongate shaft 18. A grasper tube 20 longitudinally spaces a tissue grasper ("alligator jaws") 22 from a handle 24 operated by a surgeon or other clinician. A rigid front grip 26 includes a finger opening 28 that receives one or more fingers. A movable proximal grip 30 includes a thumb opening 32 that may be drawn fore and aft to close and open the alligator jaws 22. In particular, as the movable proximal grip 30 moves distally toward the rigid front grip 26, a top portion 34 of the movable proximal grip 30 rocks away from a top portion 36 of the rigid front grip 26, retracting a grasper control rod 38 that is slidingly received within the grasper tube 20, actuating the alligator jaws 22 to a closed position.

An outer tube 40 encompasses the grasper tube 20 and is attached to the handle 24. An extrusion tube 42 is positioned within an annular recess 44 therebetween. A distal portion of the open-ended extrusion tube 42 contains the anastomosis device 16 that is thereby constrained into its straightened configuration. The grasping mechanism 12 includes a dispensing member to force the anastomosis device 16 out of the proximal end of the outer tube 40. In the illustrative version, the dispensing member, push rod 46, is slidingly received in a proximal portion of the extrusion tube 42. A slide control 48 is longitudinally slidingly engaged within a control recess 50 of the handle 24 and is attached proximally to the push rod 46 for effecting the dispensing.

In FIGS. 2-3, an alternative anastomosis instrument 60 with a similar extrusion mechanism 14 as described above includes an independently positionable grasping mechanism 62. Thus, a grasper tube 64 is slidingly received within the outer tube 40. A handle 66 is positioned with one hand that also actuates the slide control 48. The other hand positions and actuates the grasping mechanism 62. In particular, a pair of top and bottom finger holes 66, 68 are rigidly attached to a proximal end of the grasper tube 64 for longitudinally moving the alligator jaws 22. A grasper control rod 72 of the grasping mechanism 62 is proximally attached to a thumb ring 74.

Thus, with particular reference to FIG. 2, the grasper tube 64 may be extended relative to the outer tube 40 by distally pushing the finger rings 66, 68 toward the handle 66. Maintaining the thumb ring 74 proximal to the finger rings 66, 68 opens the alligator jaws 22. In FIG. 3, the finger rings 66, 68 have been drawn proximally to draw back the alligator jaws 22 close to the distal end of the outer tube 40. The thumb ring 74 has been drawn proximally relative to the finger rings 66, 68 to close the alligator jaws 22. In addition, the slide control 48 has been actuated partially to extrude a portion of the anastomosis device 16.

As depicted in FIG. 4, the flexibility of the grasping mechanism 62 is further enhanced by advantageously including a capability to form an opening through a patent tissue wall of a proximal lumen 80 in order to grasp a tissue wall of a distal lumen 82, positioning as well as holding both tissue walls 80, 82 into juxtaposition as the anastomosis clamp 16 is dispensed and engaged. For clarity, a shaft 84 formed by the grasping mechanism 62, extrusion mechanism 14 and outer tube 40 is exaggerated in transverse cross section. It should be appreciated that storing the anastomosis device 16 in a straightened configuration allows incorporating this additional capability into the shaft 84 without necessarily thickening its diameter significantly, allowing use through small openings and a small cannula (trocar) 86 to a desired anastomosis site 88 between the tissue wall of the proximal lumen 80 and the tissue wall of the distal lumen 82.

The anastomosis device 16 is transversely constrained within the outer tube 40. As previously mentioned, the anastomosis device 16 is formed from a SMA wire that is tightly coiled and annealed at a high temperature to impart a Shape Memory Effect (SME). Thus, after being straightened into a stressed shape, warming the anastomosis device 16, such as with body temperature, causes the anastomosis device 16 to relax to its tightly coiled shape as sequentially depicted in FIGS. 4A-4E. In FIGS. 4A-4B, the anastomosis device 16 has been dispensed as a substantially straight wire. The anastomosis device 16 then twists into a longitudinally spaced tapered coil in FIGS. 4C-4D. Eventually, the anastomosis device 16 longitudinally collapses into a tight coil in FIG. 4E.

It should be appreciated that at least in the first portion of this transformation, that a distal end 90 (FIG. 4A) projects substantially away from the anastomosis instrument 10, providing an opportunity for piercing and inserting by its distal movement from the anastomosis instrument 10, or by distal movement of the anastomosis instrument 10 itself. As the anastomosis device 16 becomes more fully coiled, the piercing and insertion may be advantageously accompanied by rotation of the anastomosis device 10 to adjust the number of coils that form on each side of the anastomosis site 88.

This screw-like engagement differs from some previously known cylindrical anastomosis rings that form a "hollow rivet" shape as further described in five co-pending and commonly-owned applications filed on May 20, 2003 and Sep. 30, 2003, the disclosure of each is hereby incorporated by reference in its entirety: "Bariatric Anastomosis Wire Ring Device", Ser. No. 10/443,617 to Don Tanaka; "Applier for Absorbable Fastener for Single Lumen Access Anastomosis", Ser. No. 10/675,077 to Mark Ortiz; "Unfolding Anastomosis Device", Ser. No. 10/675,091 to Jean Beaupre; "Single Lumen Access Deployable Ring for Intralumenal Anastomosis", Ser. No. 10/675,705 to Mark Ortiz; and "Single Lumen Anastomosis Applier for Self-Deploying Fastener", Ser. No. 10/675,497 to Mark Ortiz, Bill Kramer, Mike Stokes, and Foster Stulen. A great deal of clinical flexibility is provided by the presently described anastomosis device 20 in that it may be incorporated into a small diameter instrument, yet achieve a relatively large diameter non deployment. Moreover, the ability of the anastomosis device 20 to pierce a small opening in each tissue wall of lumens 16, 18 allows an opening therethrough to be of a desired size or even omitted altogether.

Figure 5:
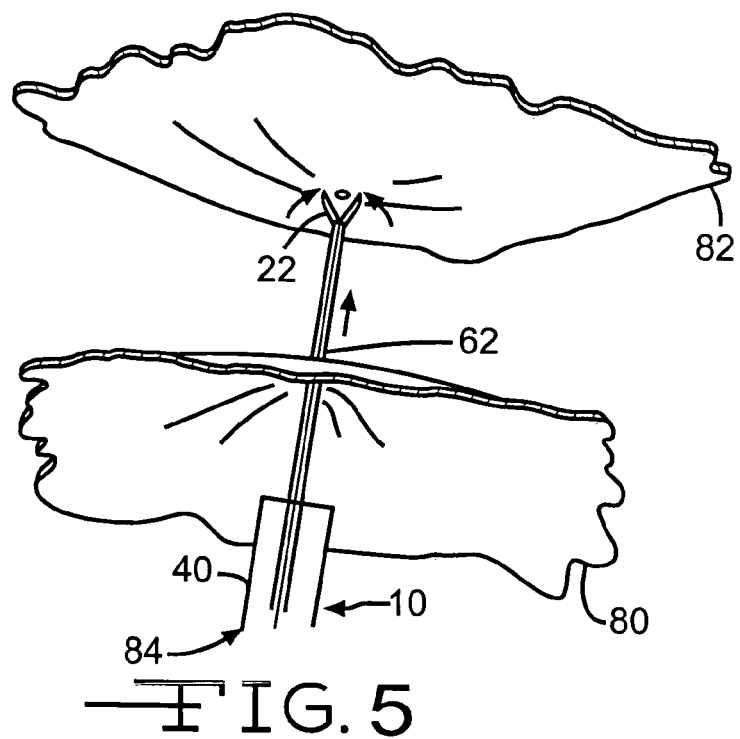
FIG. 5 is a perspective view of the anastomosis instrument of FIG. 2 employing a grasper to pierce the proximal lumen and to thereafter grasp the distal lumen.
Figure 6:
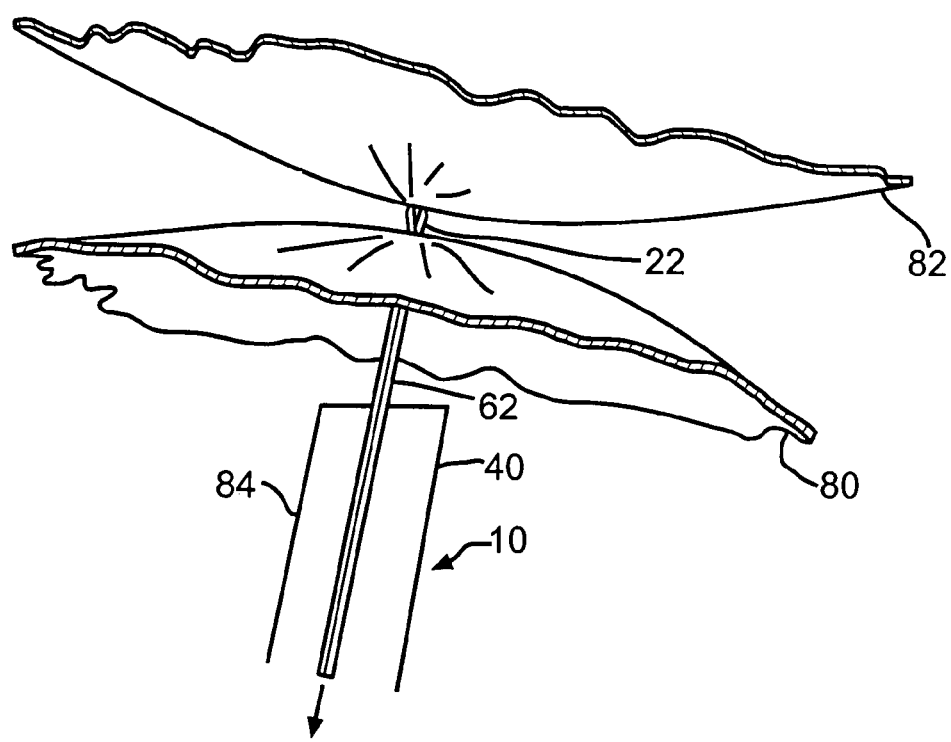
FIG. 6 is a perspective view of the anastomosis instrument of FIG. 2 employing a grasper to position the distal lumen into juxtaposition with the proximal lumen.
Figure 7:
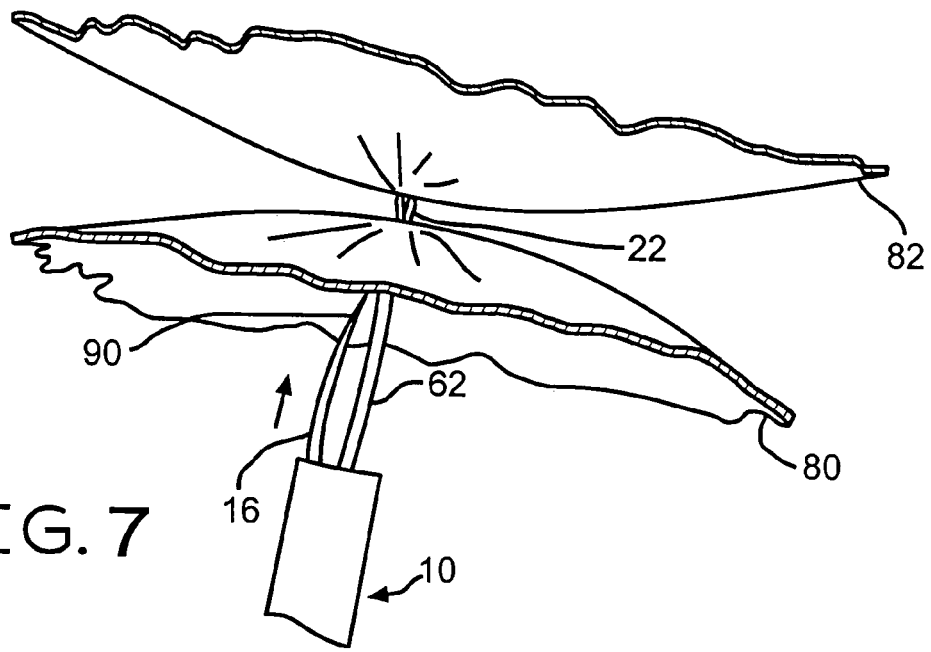
FIG. 7 is a perspective view of the anastomosis instrument of FIG. 2 grasping the distal lumen while dispensing a straightened anastomosis device.

In use, the anastomosis instrument 60 is inserted through the trocar 46 proximate to the patent tissue wall of a proximal lumen 80. With the alligator jaws 22 closed to form a piercing tip, the grasper mechanism 62 is distally advanced through the tissue wall of the proximal lumen 80 (FIG. 4). Then the alligator jaws 22 are opened to grasp the tissue wall of the distal lumen 82 (FIG. 5). The grasping mechanism 62 is drawn proximally to juxtapose the tissue walls 80, 82 (FIG. 6) and the anastomosis device 16 is distally dispensed (FIG. 7). Then the anastomosis device 8 relaxes into a coiled shape (FIG. 8) with at least one coiled portion on the distal side of the distal lumen 82 (FIG. 9) and another coiled portion on the proximal side of the proximal lumen 80 (FIG. 10). The fully relaxed anastomosis device 16 then forms the anastomosis attachment (FIG. 11).

Figure 8:
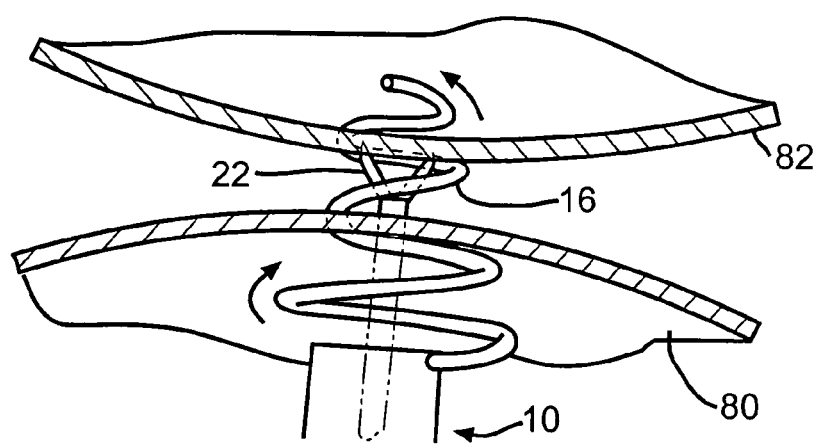
FIG. 8 is a perspective view of the anastomosis instrument of FIG. 2 grasping the distal lumen while rotating a partially coiled anastomosis device to engage the lumens.
Figure 9:
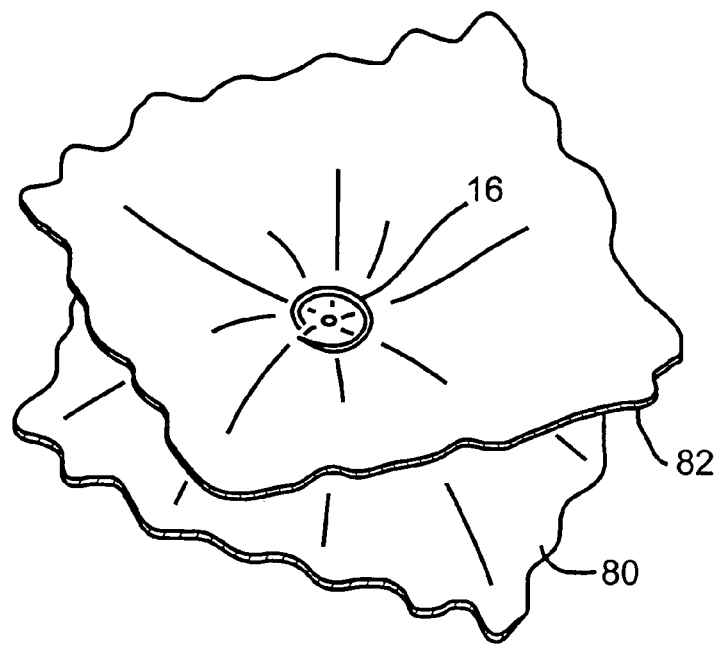
FIG. 9 is a distal perspective view of the engaged anastomosis device of FIG. 2 and the anastomosis site.
Figure 10:
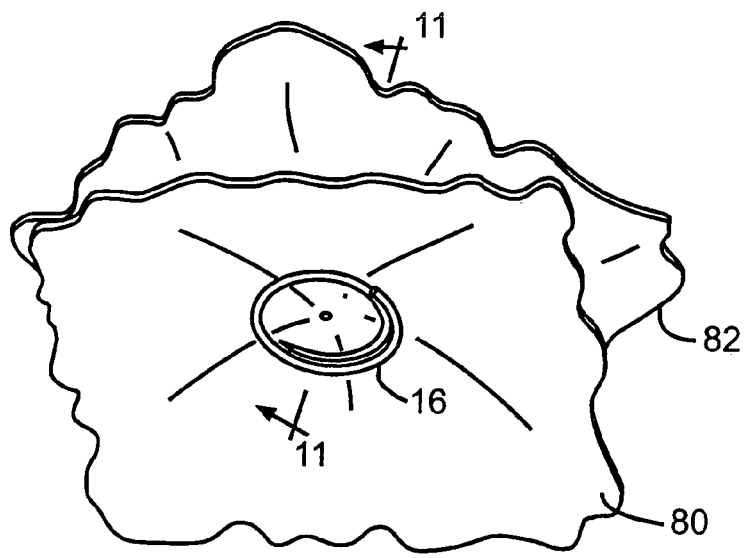
FIG. 10 is a proximal perspective view of the engaged anastomosis device of FIG. 2 and the anastomosis site.
Figure 11:
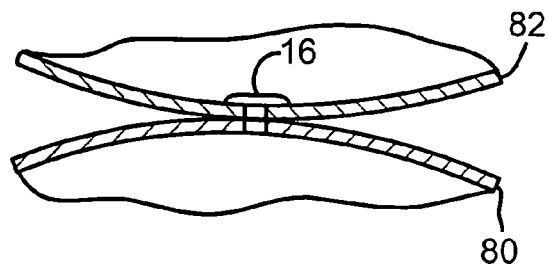
FIG. 11 is a side elevation view in cross section along lines 11-11 of FIG. 10 of the engaged anastomosis device and the anastomosis site.

With reference to FIGS. 8-10, as the anastomosis device 60 is heated by body heat, it reverts, or collapses to its originally annealed form of a tightly coiled shape (e.g., flat spiral coil, tapered coil, cylindrical coil). The desired spacing may be selected by the strength of the wire and the tightness of the coils in an unrestrained, relaxed shape, so that the tissue walls of the two lumens 80, 82 have the desired amount of pressure to achieve anastomosis without tissue damage.

It should be understood that the anastomosis device of the present invention may be used for the surgical connection of any separate or severed tubular hollow organ to form a continuous channel, such as between two parts of the intestine, or intercommunication between two or more vessels or nerves, such as the cross communication between arteries or veins, as well as other anastomosis procedures known in the art.

It will be appreciated that the terms "proximal" and "distal" are used herein with reference to a clinician gripping a handle of the anastomosis instrument 10. However, surgical instruments are used in many orientations and positions, and these terms are not intended to be limiting and absolute. In addition, aspects of the invention have application to surgical procedures performed endoscopically and laparoscopically, as well as an open procedure. Use herein of one of these or similar terms should not be construed to limit the present invention for use in only one category of surgical procedure.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For example, the anastomosis device of the present disclosure need not contain a grasper. A tool separate from the anastomosis device may be used to orient a distal lumen, or no tool may be used. Further, the grasper tube need not travel through the entire length of the outer sheath. Instead, the grasper tube may be retained within a distal portion of an outer sheath and be manipulated through wires or other means to operate as described herein.

As another example of an equivalent structure that may be used to implement the present invention, hydraulics, electronics, or pneumatics may be used to move various components relative to a handle. Moreover, an articulation mechanism may be interposed along the length of the instrument 10 to allow for increased clinical flexibility. In addition, computer control may be used with electronics and a feedback loop to move components and to selectively tension a force element based on the amount of tissue force desired. As a further example of an equivalent structure that may be used to implement the present invention, robotics could be used with the anastomosis instrument 10 attached to a controlled robotic arm that moves the entire instrument 10 or elements such as the grasper tube 32 to effect an anastomosis.

As a further example of an equivalent structure, a cannula of the anastomosis instrument may be formed of flexible materials in order to maneuver through a long lumen, such as a section of small bowel, to effect an anastomosis. Such a long, flexible tube may be used laparoscopically or endoscopically.

As a further example of an equivalent structure, instrument 10 may have a long, rigid, curved tube, or a long, rigid, straight tube, and the instrument 10 may be placed through an obturator port and used laparoscopically or endoscopically. Length and curvature becomes advantageous in endoscopic or laproscopic surgery, especially when performing a surgical procedure on a bariatric patient. In either a rigid or a flexible form of an instrument 10, restriction of gas flow through the instrument 10 becomes advantageous when maintenance of a pneumoperitoneum is desired as in, for example, endoscopic surgery.

As a further example of an equivalent structure and method that may be used to implement the present invention, the anastomosis instrument 10 may have a geometry small enough to be conveniently placed through the opening of a hand port used for hand-assisted laproscopic surgery, such as, for example, the Lap-Disk® hand port sold by Ethicon Endo-Surgery in Cincinnati, Ohio. A surgeon using the anastomosis instrument 10 through a hand port may use an endoscope through a secondary port for visualization, and may also maintain a pneumoperitoneum. The surgeon may also make use of trocars, graspers, cutters, and other endoscopic instruments inserted through auxiliary ports to assist in grasping lumens or creating otomies in lumens to perform surgical procedures such as anastomosis.

As a further example of an equivalent structure and method that may be used to implement the present invention, a long, rigid version of the anastomosis instrument 10, or a long, flexible embodiment of an anastomosis instrument may be used through an auxiliary port while tissue is manipulated by the surgeon using a hand placed through a hand port.

What is claimed is:

1. An anastomosis instrument, comprising:
   a handle;
   an elongate member having an outer tube coupled with the handle, wherein the outer tube defines a first recess, wherein the elongate member has an open distal end and defines a longitudinal axis, wherein the elongate member comprises a distal perimeter defining a distal opening at the open distal end of the elongate member such that the elongate member distally terminates at the distal perimeter defining the opening of the open distal end of the elongate member;
   a grasper tube retained within the first recess of the outer tube and coupled with the handle, wherein the grasper tube defines a first axis;
   an extrusion tube retained within the first recess of the outer tube adjacent the grasper tube, wherein the extrusion tube defines a second axis that is separate from the first axis defined by the grasper tube, wherein the extrusion tube is external to the grasper tube, wherein the extrusion tube has an open distal end, wherein the extrusion tube comprises a distal perimeter defining a distal opening at the open distal end of the extrusion tube such that the extrusion tube distally terminates at the distal perimeter defining the opening of the open distal end of the extrusion tube;
   an anastomosis device configured to provide a continuous channel from a first tissue lumen to a second tissue lumen, wherein the anastomosis device is formed from a shape memory alloy wire annealed in a coil shape and longitudinally straightened, wherein the anastomosis device is loaded within the extrusion tube in a substantially straight configuration prior to deployment;
   a second recess formed in the outer tube of the elongate member, wherein the second recess is located proximate to the handle;
   a proximally actuated slide control slidingly received in the second recess formed in the outer tube of the elongate member, wherein the slide control is operable to distally dispense the anastomosis device through the distal opening of the extrusion tube and through the distal opening of the elongate member in a direction substantially parallel to the longitudinal axis;
   a pair of grasping jaws, the pair of grasping jaws being configured to extend distally beyond the distal opening of the elongate member and being operable in an open position and a closed position, wherein in the closed position the pair of grasping jaws comprise a piercing tip to penetrate a first layer of tissue defining the first tissue lumen and wherein in the open position the pair of grasping jaws are configured to grasp a second layer of tissue defining the second tissue lumen; and
   a grasper control mechanism operably coupled to the pair of grasping jaws through the grasper tube to effect opening and closing of the grasping jaws, wherein the grasper control mechanism is further operable to move the grasping jaws longitudinally through a range of motion distal to the distal opening of the elongate member.

2. The anastomosis instrument of claim 1, wherein the coil shape comprises a flattened coil.

3. The anastomosis instrument of claim 1, wherein the coil shape comprises a tapered coil.

4. The anastomosis instrument of claim 1, wherein the coil shape comprises a cylindrical coil.

5. The anastomosis instrument of claim 1, wherein the shape memory alloy comprises nitinol 6. An anastomosis instrument for implanting an anastomosis device formed from a shape memory alloy wire annealed in a coil shape and longitudinally stretched with one end distally projecting forming a stressed shape, the anastomosis instrument comprising:

an elongate member having an outer tube coupled with a handle, wherein the outer tube defines an annular recess, wherein the elongate member has an open distal end, wherein the elongate member comprises a distal perimeter defining a distal opening at the open distal end of the elongate member such that the elongate member distally terminates at the distal perimeter defining the opening of the open distal end of the elongate member;

a grasper tube retained within the annular recess of the outer tube and coupled with the handle, wherein the grasper tube defines a first axis;

an extrusion tube, the extrusion tube being coupled to the outer tube and positioned within the annular recess of the outer tube adjacent the grasper tube, wherein the extrusion tube defines a second axis that is separate from and parallel to the first axis defined by the grasper tube, wherein the extrusion tube is external to the grasper tube, wherein the extrusion tube is configured to receive the anastomosis device in a substantially longitudinally straight configuration, wherein the extrusion tube has an open distal end, wherein the extrusion tube comprises a distal perimeter defining a distal opening at the open distal end of the extrusion tube such that the extrusion tube distally terminates at the distal perimeter defining the opening of the open distal end of the extrusion tube;

a proximally actuated slide control slidingly received in the elongate member, wherein the slide control is operable to distally dispense the anastomosis device distally out through the distal opening of the elongate member;

a pair of pivotally coupled grasping jaws, the pair of grasping jaws being configured to extend distally out through the distal opening of the elongate member and being operable in an open position and a closed position, wherein in the closed position the pair of grasping jaws comprise a piercing tip to penetrate a first layer of tissue defining a first tissue lumen and wherein in the open position the pair of grasping jaws are configured to grasp a second layer of tissue defining a second tissue lumen; and a grasper control mechanism coupled to the pair of grasping jaws, wherein the grasper control mechanism comprises a jaw positioning member longitudinally received through the grasper tube, wherein the jaw positioning member is operable to effect opening and closing of the grasping jaws when the grasping jaws are positioned distal to the open distal end of the elongate member.

* * * * *